United States Patent
Rui et al.

(10) Patent No.: US 10,119,924 B2
(45) Date of Patent: Nov. 6, 2018

(54) COMPUTED TOMOGRAPHY WITH DETECTOR WOBBLE

(71) Applicant: General Electric Company, Schenectady, NY (US)

(72) Inventors: Xue Rui, Clifton Park, NY (US); Geng Fu, Clifton Park, NY (US); Jianjun Guo, Ballston Spa, NY (US); Bruno Kristiaan Bernard De Man, Clifton Park, NY (US); Brian David Yanoff, Schenectady, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 212 days.

(21) Appl. No.: 15/087,560

(22) Filed: Mar. 31, 2016

(65) Prior Publication Data
US 2017/0285188 A1    Oct. 5, 2017

(51) Int. Cl.
G01N 23/046 (2018.01)
G01T 1/17 (2006.01)
G01T 1/29 (2006.01)
G01N 23/083 (2018.01)

(52) U.S. Cl.
CPC ......... *G01N 23/046* (2013.01); *G01N 23/083* (2013.01); *G01T 1/17* (2013.01); *G01T 1/2985* (2013.01); *G01N 2223/505* (2013.01)

(58) Field of Classification Search
CPC ..... G01T 1/247; G01T 1/2018; G01N 23/046; G01N 2223/505
USPC ....................................................... 250/361
See application file for complete search history.

(56) References Cited

U.S. PATENT DOCUMENTS

| | | |
|---|---|---|
| 5,323,007 A | 6/1994 | Wernick et al. |
| 5,841,829 A | 11/1998 | Dolazza et al. |
| 6,047,040 A | 4/2000 | Hu et al. |
| 6,411,670 B1 | 6/2002 | Besson |
| 6,963,631 B2 | 11/2005 | Brunnett |
| 7,488,945 B2 | 2/2009 | Li et al. |

FOREIGN PATENT DOCUMENTS

WO    2014107651 A1    7/2014

OTHER PUBLICATIONS

Hsieh et al., "Reconstruction technique for focal spot wobbling", SPIE Proceedings, vol. 1652, Jun. 1992.
Ulzheimer et al., "Multislice CT: Current Technology and Future Developments", pp. 14 of 23, 2009.
Voland et al., "Novel Techniques for High-Resolution Computed Tomography of Optoelectronic Devices", http://www.ndt.net/article/wcndt2012/papers/119_wcndtfinal00119.pdf, pp. 7 of 11.

*Primary Examiner* — David Porta
*Assistant Examiner* — Gisselle Gutierrez
(74) *Attorney, Agent, or Firm* — GE Global Patent Operation; Pabitra Chakrabarti

(57) ABSTRACT

The present approach relates to a detector design that allows detector-based wobble using an electronic control scheme. In one implementation, each detector pixel is divided into sub-pixels. The readout of the sub-pixels can be binned with minimal noise penalty to enable the detector wobble without physically shifting the detector or alternating the physical focal spot location, though, as discussed herein alternation of the focal spot location may be used in conjunction with the present approach to further improve radial and longitudinal imaging resolution as well as suppressing artifacts resulted by limited spatial sampling.

15 Claims, 13 Drawing Sheets

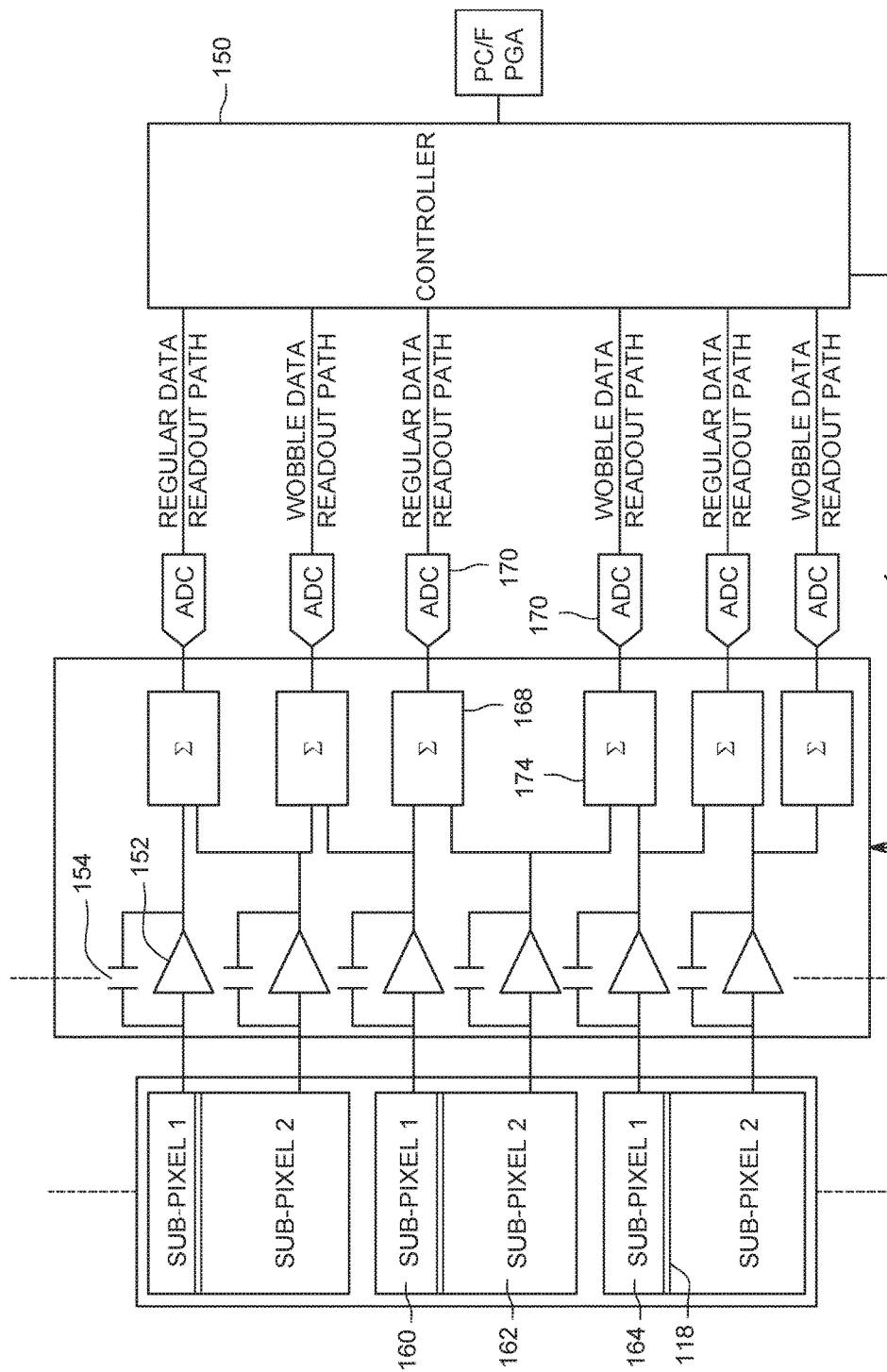

COMPUTED TOMOGRAPHY WITH DETECTOR WOBBLE

BACKGROUND

The subject matter disclosed herein relates to the fabrication and use of radiation detectors, including X-ray radiation detectors, configured for use in high resolution imaging contexts.

Non-invasive imaging technologies allow images of the internal structures or features of a subject (patient, manufactured good, baggage, package, or passenger) to be obtained non-invasively. In particular, such non-invasive imaging technologies rely on various physical principles, such as the differential transmission of X-rays through the target volume or the reflection of acoustic waves, to acquire data and to construct images or otherwise represent the internal features of the subject.

Computed Tomography (CT) scanners operate by projecting fan-shaped or cone-shaped X-ray beams from an X-ray source. The X-ray source emits X-rays at numerous view angle positions about an object being imaged, such as a patient, which attenuates the X-ray beams as they traverse the object. The attenuated beams are detected by a set of detector elements which produce signals representing the intensity of the incident X-ray beams. The signals are processed to produce data representing the line integrals of the linear attenuation coefficients of the object along the X-ray paths. These signals are typically called "projection data" or just "projections". A 3D image volume of the imaged object can be reconstructed using different reconstruction techniques, such as filtered-back projection, to allow the visualization of the internal structures. The images may in turn be associated to represent a volume or volumetric rendering of a region of interest. In a medical context, pathologies or other structures of interest may then be located or identified from the reconstructed image volume.

In certain imaging contexts, it is desirable to introduce a focal spot "wobble" mode in a given CT system. Such an operation mode typically involves alternating between two or more spatially offset focal spot locations on an X-ray generating target at some or all of the view angles. Such a wobble can be applied to both radial and longitudinal directions in a CT system to improve in-plane and z-direction spatial resolution as well as reducing the aliasing artifacts with improved spatial sampling, effectively increasing the number of projections views for each gantry rotation.

BRIEF DESCRIPTION

In one embodiment, a radiation detector is provided. In accordance with this embodiment, the radiation detector includes a plurality of pixels. Each pixel includes: a scintillator material that emits optical photons when exposed to X-rays; at least two photodetector elements, each photodetector element corresponding to a sub-pixel of the respective pixel, wherein each photodetector element is configured to generate electrical signals in response to the emitted optical photons that impact respective photodetector elements; at least two signal summing circuits, wherein each signal summing circuit takes analog signals from at least two sub-pixels and produces a digital signal representing a linear combination of the signals from the two sub-pixels, wherein the signal summing circuits possess at least two summing modes, wherein at least one summing mode combines analog signals from sub-pixels within the same pixel and at least one summing mode combines analog signals from sub-pixels in different pixels; and a controller configured to assign the summing mode of the summing circuits.

In a further embodiment, a plurality of sub-pixels of a radiation detector are read out in an alternating manner in which: during a regular readout operation, separately acquiring a first analog signal from a first sub-pixel and a second analog signal from a second sub-pixel adjacent to the first sub-pixel in a first direction and summing the first analog signal and the second analog signal to generate a summed regular pixel digitized signal; and during a wobble readout operation, separately acquiring a fourth analog signal from the first sub-pixel and a third analog signal from a third sub-pixel adjacent to the first sub-pixel in a second direction and summing the fourth analog signal and the third analog signal to generate a summed wobble pixel digitized signal.

In an additional embodiment, a radiation detector is provided. In accordance with this embodiment, the radiation detector includes: a plurality of pixels, each pixel divided into a first sub-pixel and a second sub-pixel; a readout path for each first sub-pixel and second sub-pixel, wherein each readout path is available for a first state in which outputs of the first sub-pixel and the second sub-pixel of the same respective pixels are combined and a second state in which outputs of the first sub-pixel and the second sub-pixel of different pixels are combined; a controller configured to assign the readout paths between the first state and the second state during operation; and an ASIC configured to allow integration of the readout signal so that the summed signal from different summing locations can be readout simultaneously.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 11 depicts a circuit-based view of the readout arrangement for a detector, in accordance with aspects of the present disclosure;

DETAILED DESCRIPTION

Figure 1:
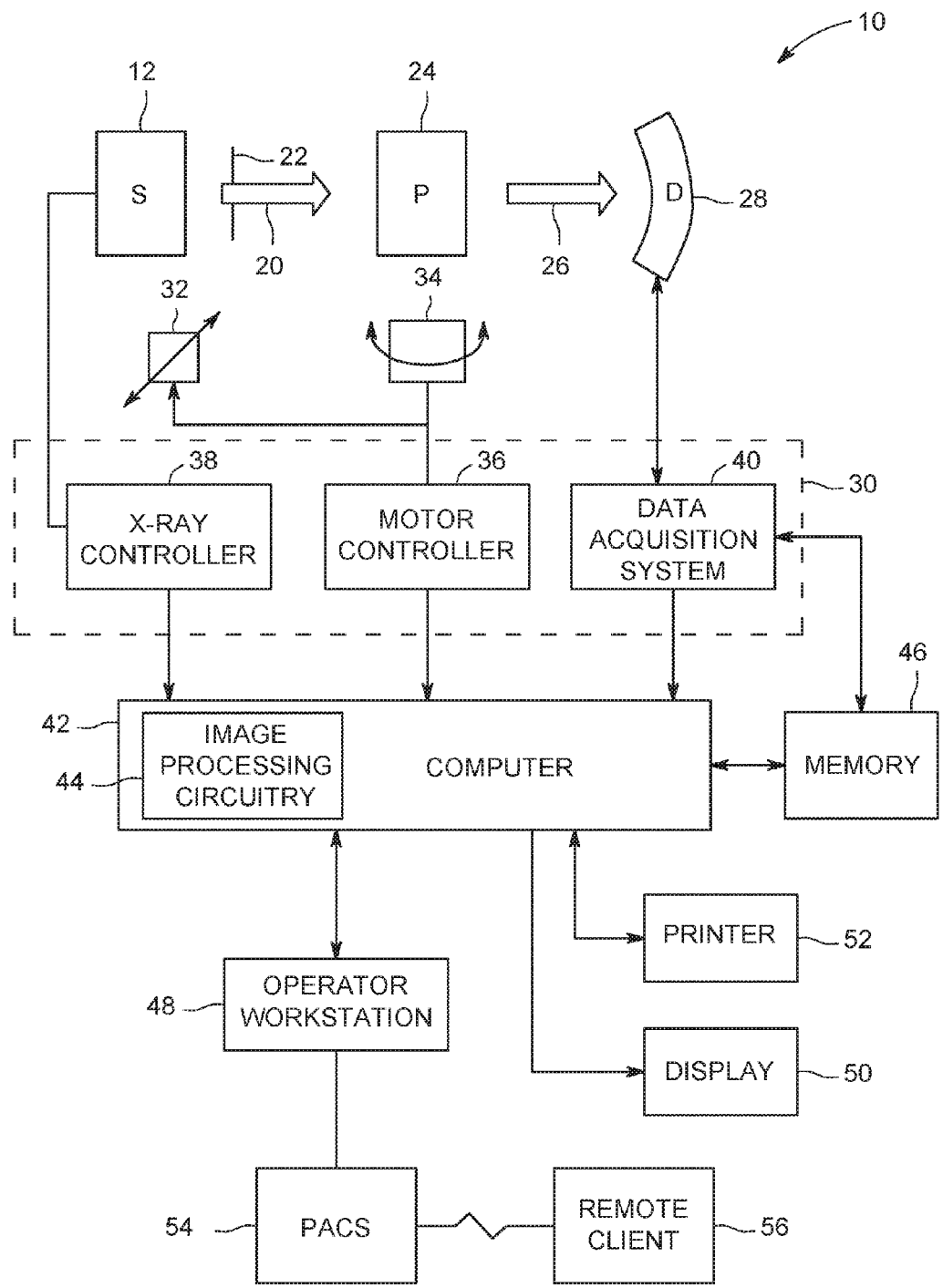
FIG. 1 is a schematic illustration of an embodiment of a Computed Tomography (CT) system configured to acquire projection data of a patient and to process the data in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

While the following discussion is generally provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

The present approach relates to a detector design that may be used to enable detector wobble using an electronic control scheme with a controlled readout pattern. In this manner, spatial sampling may be increased without physically moving the focal spot or the detector but only by electronic control of the readout pattern of the detector pixels. In one implementation, each detector pixel is divided into sub-pixels. The readout of the sub-pixels can be binned with minimal electronic noise penalty to enable the detector wobble without physically shifting the detector or alternating the physical focal spot location, though, as discussed herein alternation of the focal spot location may be used in conjunction with the present approach to further improve radial and longitudinal spatial sampling. The signal from two readout patterns can be obtained at the same time which further reduces the measurement time and provides improved temporal resolution.

In certain embodiments, the radiation detector employed may be fabricated as a tiled silicon wafer based detector and using complementary metal-oxide-semiconductors (CMOS) technology. In particular, fabrication and use of a radiation detector as discussed herein may, in certain implementations, utilize electronic readout circuitry that is integrated with the respective photodetectors on a single wafer (e.g., c-Si wafer or die) using CMOS technology. In certain such implementations, the integrated readout electronics reduces or minimizes parasitic impedance, thereby reducing associated noise, and correspondingly offers better noise performance in certain applications, including the binning operations discussed herein that are used to achieve the described wobble mode.

In particular, in certain implementations described herein the low-noise characteristics of the integrated readout electronics may facilitate certain binning operations or actions, such as grouping (i.e., binning) of sub-pixels during a scanning operation employing detector-based wobble. In particular, the integrated readout electronics in such implementations may facilitate manipulation of the readout operations at the detector to achieve the wobble mode. In this manner, a suitably configured detector, which may or may not include and use integrated readout electronics as discussed herein, may be used adaptively to introduce a wobble mode. Such detector-based wobble modes may or may not be performed in conjunction with actual alternation between spatially offset focal spot target locations, depending on the implementation.

With the preceding discussion in mind, FIG. 1 illustrates an embodiment of an imaging system 10 for acquiring and processing image data in accordance with aspects of the present disclosure. In the illustrated embodiment, system 10 is a Computed Tomography (CT) system designed to acquire X-ray projection data, to reconstruct the projection data into a tomographic image volume, and to process the image data for display and analysis. Though CT imaging technique is discussed herein, other imaging modalities may also benefit from the present radiation detector design. The depicted CT imaging system 10 includes an X-ray source 12. As discussed in detail herein, the source 12 may include one or more X-ray sources, such as an X-ray tube or one or more enclosures containing solid state emission structures. The X-ray source 12, in accordance with certain contemplated embodiments, is configured to emit an X-ray beam 20 from one or more emission spots (including spatially offset focal spots), which may correspond to X-ray emission regions on a target structure (e.g., an anode structure) impacted by a directed electron beam.

In certain implementations, the source 12 may be positioned proximate to a filter assembly or beam shaper 22 that may be used to steer the X-ray beam 20, to define the shape and/or extent of a high-intensity region of the X-ray beam 20, to control or define the energy profile of the X-ray beam 20, and/or to otherwise limit X-ray exposure on those portions of the patient 24 not within a region of interest. In practice, the filter assembly or beam shaper 22 may be incorporated within the gantry between the source 12 and the imaged volume.

The X-ray beam 20 passes into a region in which the subject (e.g., a patient 24) or object of interest (e.g., manufactured component, baggage, package, and so forth) is positioned. The subject attenuates at least a portion of the X-rays 20, resulting in attenuated X-rays 26 that impact a detector array 28 formed by a plurality of detector elements (e.g., pixels or sub-pixels) as discussed herein. Each detector element produces an electrical signal that represents the intensity of the X-ray beam incident at the position of the detector element when the beam strikes the detector 28. Electrical signals are acquired and processed to generate one or more scan datasets. In certain implementations discussed herein, the detector 28 may include integrated readout circuitry and control logic, facilitating the output of digitized signals to downstream components and the binning of alternating combinations of sub-pixels of the detector 28 to achieve a detector-based wobble mode. In the depicted example, the detector 28 is coupled to the system controller 30, which commands acquisition of the digital signals generated by the detector 28.

A system controller 30 commands operation of the imaging system 10 to execute filtration, examination and/or calibration protocols, and to process the acquired data. With respect to the X-ray source 12, the system controller 30 furnishes power, focal spot location, control signals and so forth, for the X-ray examination sequences. In accordance with certain embodiments, the system controller 30 may control operation of the filter assembly 22, the CT gantry (or other structural support to which the X-ray source 12 and detector 28 are attached), and/or the translation and/or inclination of the patient support over the course of an examination.

In addition, the system controller 30, via a motor controller 36, may control operation of a linear positioning subsystem 32 and/or a rotational subsystem 34 used to move components of the imaging system 10 and/or the subject 24. The system controller 30 may include signal processing circuitry and associated memory circuitry. In such embodiments, the memory circuitry may store programs, routines, and/or encoded algorithms executed by the system controller 30 to operate the imaging system 10, including the X-ray source 12 and/or filter assembly 22, and to process the digital measurements acquired by the detector 28 in accordance with the steps and processes discussed herein. In one embodiment, the system controller 30 may be implemented as all or part of a processor-based system.

The source 12 may be controlled by an X-ray controller 38 contained within the system controller 30. The X-ray controller 38 may be configured to provide power, timing signals, and/or focal size and spot locations to the source 12. In addition, in some embodiments the X-ray controller 38 may be configured to selectively activate the source 12 such that tubes or emitters at different locations within the system 10 may be operated in synchrony with one another or independent of one another or to switch the source between different energy profiles during an imaging session.

The system controller 30 may include a data acquisition system (DAS) 40. The DAS 40 receives data collected by readout electronics of the detector 28, such as digital signals from the detector 28. The DAS 40 may then convert and/or process the data for subsequent processing by a processor-based system, such as a computer 42. In certain implementations discussed herein, circuitry within the detector 28 may convert analog signals of the photodetector to digital signals prior to transmission to the data acquisition system 40. The computer 42 may include or communicate with one or more non-transitory memory devices 46 that can store data processed by the computer 42, data to be processed by the computer 42, or instructions to be executed by a processor 44 of the computer 42. For example, a processor of the computer 42 may execute one or more sets of instructions stored on the memory 46, which may be a memory of the computer 42, a memory of the processor, firmware, or a similar instantiation.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data, contrast agent density maps produced in accordance with the present disclosure, and so forth. Additionally, the system 10 may include a printer 52 coupled to the operator workstation 48 and configured to print any desired measurement results. The display 50 and the printer 52 may also be connected to the computer 42 directly or via the operator workstation 48. Further, the operator workstation 48 may include or be coupled to a picture archiving and communications system (PACS) 54. PACS 54 may be coupled to a remote system 56, radiology department information system (RIS), hospital information system (HIS) or to an internal or external network, so that others at different locations can gain access to the image data.

Figure 2:
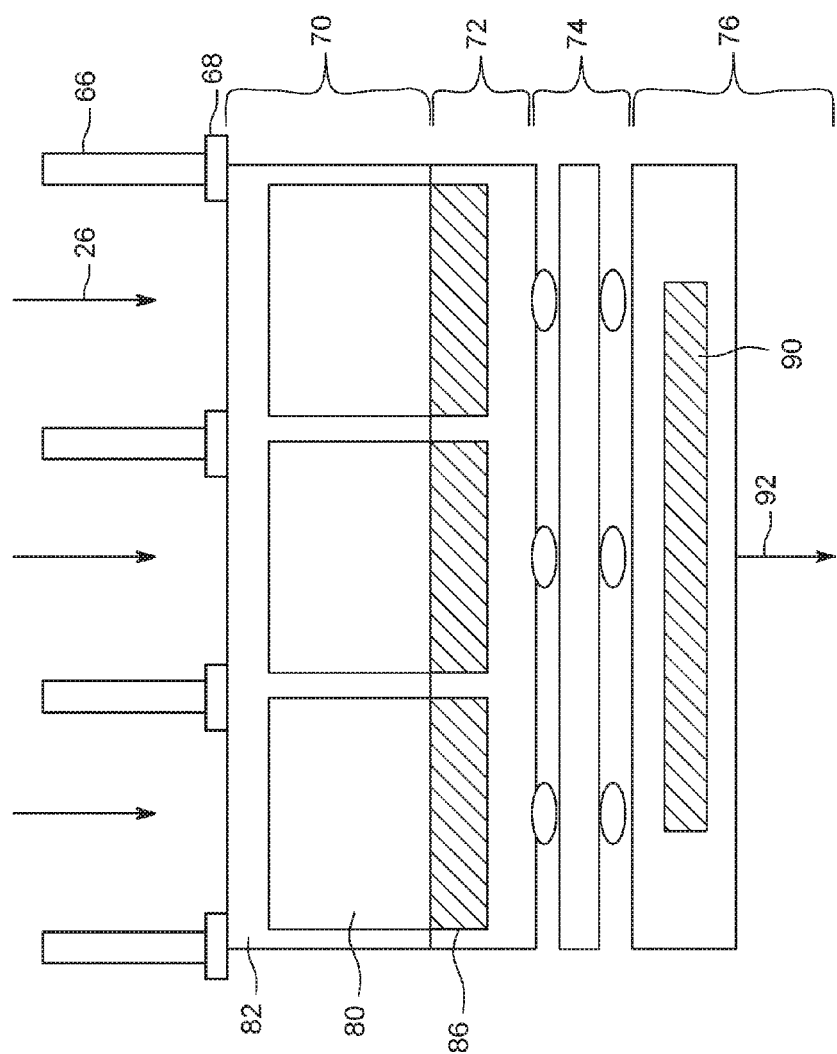
FIG. 2 depicts a cross-sectional view of components of a prior art radiation detector.
Figure 3:
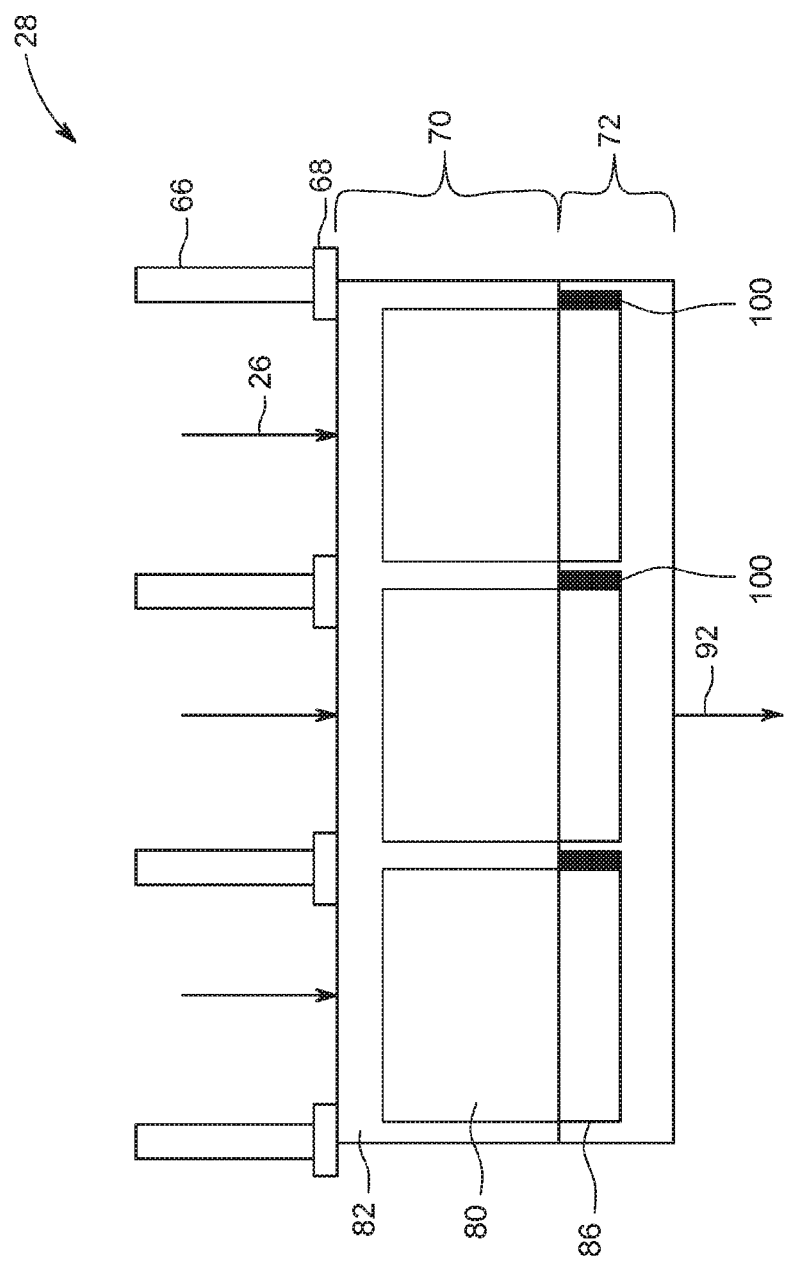
FIG. 3 depicts a cross-sectional view of components of a radiation detector having integrated readout electronics, in accordance with aspects of the present disclosure.
Figure 4:
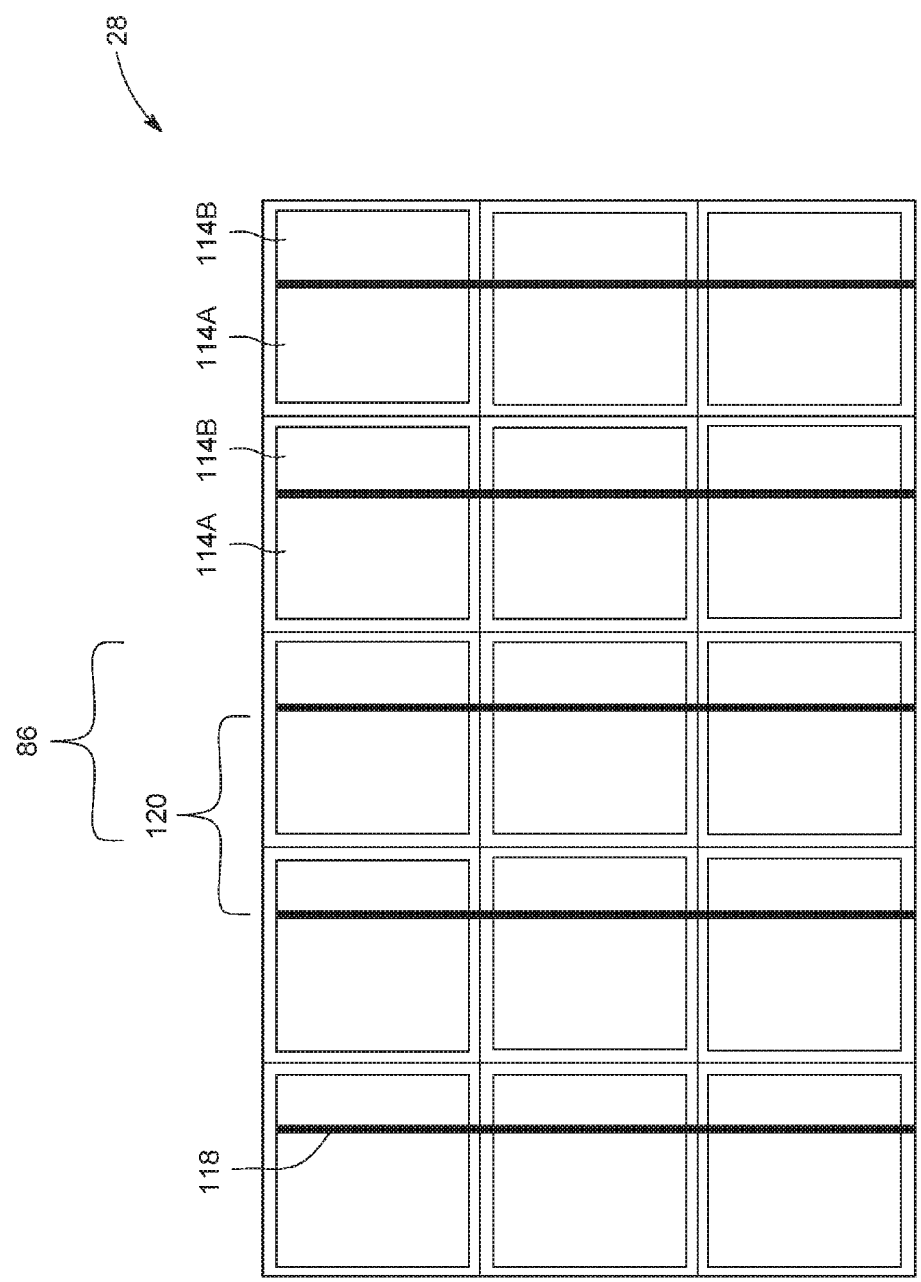
FIG. 4 depicts a top-down view of one sub-pixel configuration of a detector panel, in accordance with aspects of the present disclosure.
Figure 5:
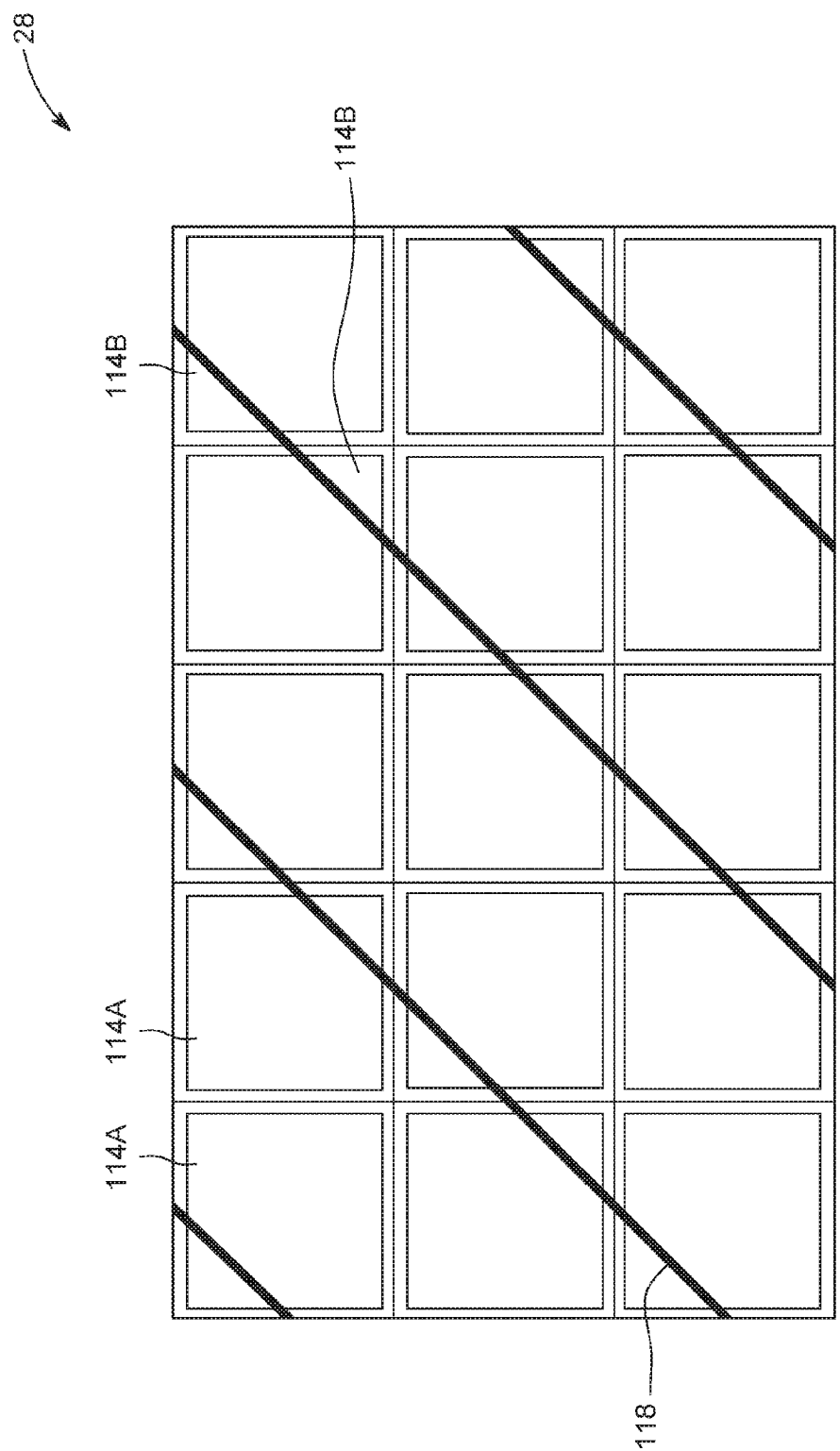
FIG. 5 depicts a top-down view of another sub-pixel configuration of a detector panel, in accordance with aspects of the present disclosure.

With the preceding discussion of an overall imaging system 10 in mind, a brief discussion of aspects of the detector 28, including its fabrication and use, are further developed in FIGS. 2-4. In particular, FIGS. 2 and 3 illustrate structural elements of a conventional detector and a detector incorporating readout electronics on the light imager panel, which may be useful in certain contexts described herein for binning different combinations of sub-pixels to achieve a wobble effect. FIGS. 4 and 5, in turn, depict plan or top-views of sub-pixels arrangements that may be useful to achieve the described detector-based wobble effect, regardless of whether integrated readout electronics are employed or not.

With the preceding in mind, and turning to FIG. 2, a conventional detector arrangement is provided so as to better distinguish aspects of the present approach. In particular, FIG. 2 depicts a schematic view of a conventional X-ray detector in cross section. The depicted conventional radiation detector of FIG. 2 has certain features in common with, and other features distinct from, certain implementations of the radiation detector 28 discussed herein.

The depicted detector of FIG. 2 includes a radiation stopping or conversion layer 70, a light imager panel or layer 72 (typically provided as an array of photodetector element, e.g., pixels or sub-pixels), a conductive path 74, and readout circuitry 76 configured to readout the light imager panel 72 but provided off-panel with respect to the light imager panel 72. Also depicted are a collimator 66 (e.g., anti-scatter grid) and associated grid plate 68 which may be present to reduce the number of scattered X-ray photons that are incident on the scintillation material 80.

The radiation stopping or conversion layer 70 typically may be provided as a layer of monolithic (i.e., continuous) or pixelated scintillation material 80 that emits lower-energy photons (e.g., optical wavelength photons) when exposed to higher-energy photons 26 (e.g., X-ray or gamma-ray photons). In the depicted example, the scintillation material 80 is pixelated, being separated into individual elements by a light reflecting material 82 that also covers the scintillation material 80 to reduce loss of useful signal.

Low-energy photons emitted by the conversion layer 70 are detected at the light imager panel 72. In particular, the light imager panel 72 typically comprises photodiodes defining an array of photodetector elements (which may correspond to pixels 86 or sub-pixels). Optical photons incident on the photodetector elements result in charge being developed at the respective pixels 86 or sub-pixels which, when read out, corresponds to the incidence of X-rays (or gamma rays) at that location on the detector 28.

The charges at the respective pixels 86 are readout and reset by respective readout circuitry 76 (typically provided as one or more application specific integrated circuits—

ASICs 90) that is typically fabricated off-panel with respect to the pixels 86 and which is electrically connected by conductive paths 74 in the form of flex circuitry, bump bonds, or other electrical interconnections. The readout circuitry (e.g., ASICs 90) may include circuitry for amplifier and analog-to-digital conversion (ADC), yielding digital signal 92 that is output from the readout circuitry 76 for subsequent processing.

The detector shown in FIG. 2, while providing useful radiation detection measurements, is notably complex in construction (requiring numerous electrical interconnections between components), with the 3D packaging adding to the cost and degrading performance due to the large interconnect capacitance. Thus, substantial noise may be introduced to the measurements due to the length and nature of the electrical interconnect structures and the distance that the analog signal is propagated before digital conversion.

Turning to FIG. 3, in accordance with the certain implementations of the present approach employing a detector 28 having integrated readout electronics, a detector 28 is provided that is simpler in design than the conventional detector shown in FIG. 2 and is suitable for performing alternating pixel or sub-pixel binning operations at the level of the detector. In particular, the detector 28 of FIG. 3 includes integrated readout electronics 100 provided in the light imager panel 72 itself. Such an arrangement simplifies the overall design of the detector 28 and also reduces introduced electronic noise by eliminating the conductive structures 74 (FIG. 1) used to transmit analog signals to the readout and conversion circuitry located off-panel in conventional designs. In this manner, a digital output 92 is output by the light imager panel 72 itself, rather than being generated at an off-panel module. As shown in the depicted example of FIG. 3, the integrated readout electronics 100 is fabricated in the silicon region directly underneath the collimator 66 and grid plate 68, thus shielding the electronics 100 from incident radiation and reducing or eliminating the risk of radiation damage to the electronics 100. While the cross-sectional side-view of detector 28 depicts aspects related to the integration of readout electronics 100 onto the light imager panel 72, further aspects of the detector 28 related to implementing a detector-based wobble mode are discussed and illustrated in greater detail below. Further, as noted above, though a detector 28 having integrated readout electronics may be suitable for performing detector-based wobble imaging as discussed herein, such integrated readout electronics are not necessary in all implementations and merely represent one suitable electrical configuration of the components of the detector 28 for performing such wobble operations.

As discussed herein, in certain implementations the detector elements (encompassing both pixels 86 and sub-pixels 114 as used herein) may be alternately binned during operation using integrated readout electronics 100 or other suitable readout approaches. In one implementation, the binning operation is performed so as to achieve a wobble effect at the detector that is equivalent or comparable to what would be achieved by alternating a spatial location of a focal spot on a target of the X-ray source.

Figure 6:
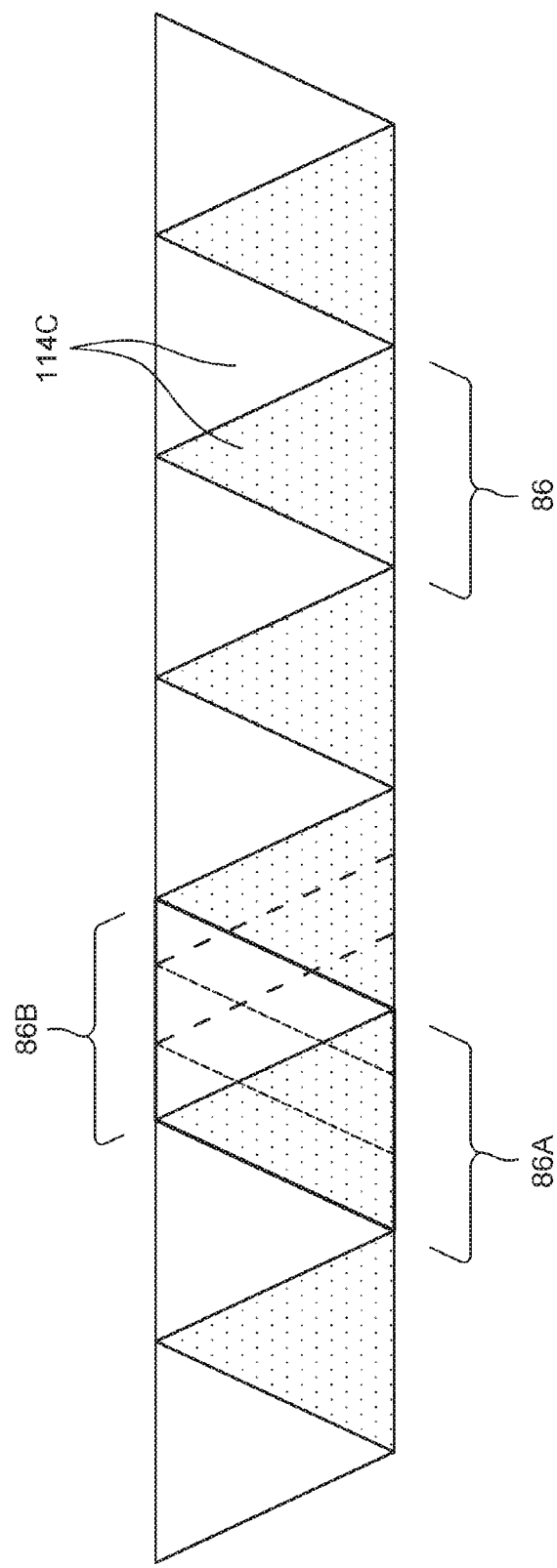
FIG. 6 depicts a top-down view of a further sub-pixel configuration of a detector panel, in accordance with aspects of the present disclosure.

Turning to FIGS. 4-6, top-down views of a detector 28 or a portion of such a detector are provided having different configurations of sub-pixels 114 (e.g., large sub-pixels 114A and smaller sub-pixels 114B) into which each pixel 86 is divided. In the depicted example, sub-pixels 114 may be formed by a linear (i.e., straight) cut 118, such as a wire or blade cut) through the scintillator 80. In the depicted example, the linear cuts 118 may constitute an air gap or may be filled with or otherwise include a reflector so as to help channel optical signal to the defined sub-pixel region. As discussed in greater detail below, the adjacent large and small sub-pixels 114A and 114B may be readout or binned and read out in an alternating manner (e.g., as pixel 86 and offset "pixel" 120) so as electronically achieve a wobble mode by manipulation of the readout of the detector 28 alone.

Turning to FIG. 5, an alternate arrangement of linear cuts 118 is shown which diagonally cut each pixel 86 into larger sub-pixels 114A and smaller sub-pixels 114B. In such an example, the smaller sub-pixels 114B effectively are triangular sub-pixels while the larger sub-pixels 114B are square pixels from which a triangular region has been removed. In this manner, alternating combination of smaller, triangular sub-pixels 114B with adjacent larger sub-pixels 114A still effectively provides a constant pixel area for the alternate readout combinations. As in the preceding example, each cut 118 (such as a wire or blade cut through the scintillator 80) may be provided as an unfilled air gap or may include a reflector in the final detector 28 configuration. Such a diagonal cut provides the smaller sub-pixel for signal with high spatial resolution information while minimizing the reduction of the fill-fraction factor which is caused by the reduction of the active area on the pixel surface from the unfilled air gap or reflector.

In FIG. 6, an alternative pixel/sub-pixel arrangement is depicted in which the sub-pixels 114C have a triangular geometry, and thus the combination of two-sub-pixels forms a trapezoidal pixel 86 as opposed to a conventional square or rectangular pixel. Such an arrangement provides additional flexibility with respect to combinations of sub-pixels 114 as discussed herein in that a given triangular sub-pixel 114C can be recombined with adjacent triangular sub-pixels 114C in an equivalent manner in terms of the exposed surface area exposed to radiation resulting from the combination. Thus, a wobble mode may be accomplished in accordance with the approaches described herein, as discussed below. By way of example, and as shown in FIG. 6, a first combination of triangular sub-pixels 114C may correspond to what is deemed a normal pixel 86A, while a second combination of sub-pixels 114C, having a shared triangular sub-pixel, may be deemed a wobble pixel 86B.

With these various sub-pixel 114 arrangements in mind, FIGS. 7-10 depict different implementations for using certain of the described sub-pixel arrangements to achieve a detector-based wobble effect during imaging. In these examples, the sub-pixel 114 arrangement shown in FIG. 4 is depicted so as to simplify presentation, though it should be appreciated that the described approach will also be suitable for use with other sub-pixel configurations, including the configurations shown in FIGS. 5 and 6.

Figure 7:
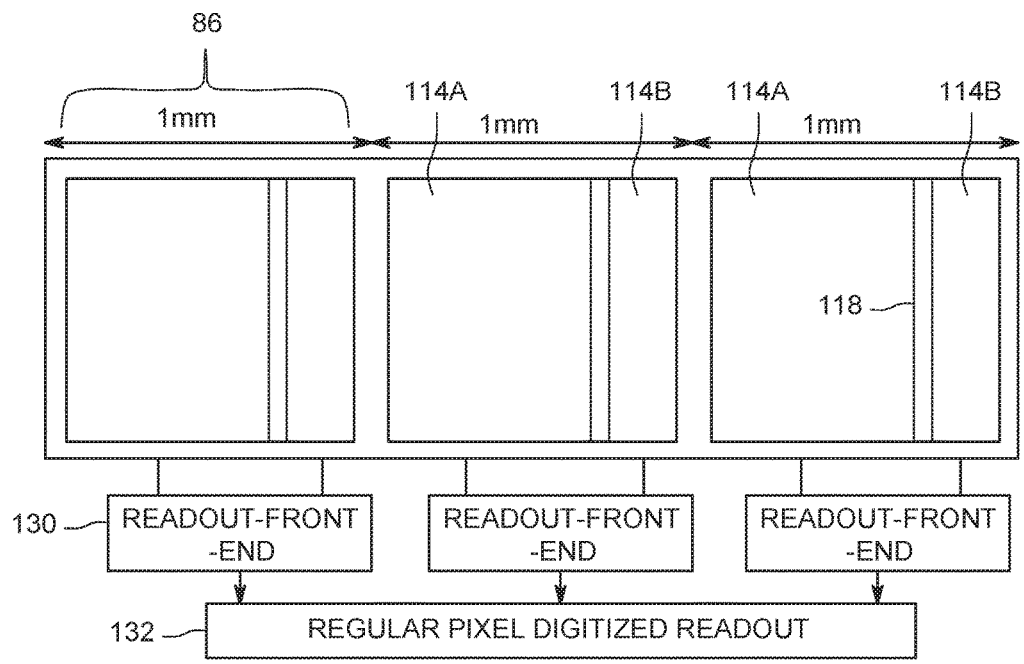
FIG. 7 depicts a first readout configuration for a detector in regular readout mode, in accordance with aspects of the present disclosure.
Figure 8:
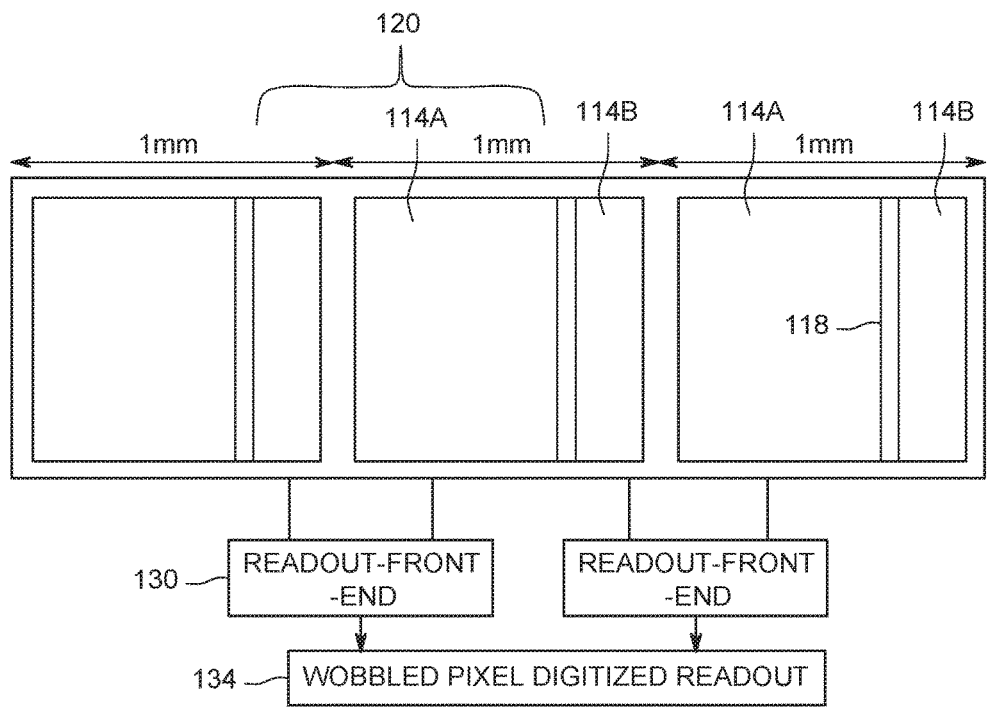
FIG. 8 depicts a second readout configuration for a detector in wobble readout mode, in accordance with aspects of the present disclosure.

With respect to the differing implementations, different approaches are shown whereby signal from different paired combinations of large and small sub-pixels (or equally sized sub-pixels, such as shown in FIG. 6) may be combined so as to effectively be reading out two proximate, but offset pixels. In this manner, electronic control of the readout operation provides a wobble mode corresponding to alternating focal spot locations of an X-ray source. The detector-based wobble approach may be accomplished using differing binning schemes. In implementations in which the detector 28 includes integrated readout electronics as part of the light imager panel 72, as discussed above, the signals from the sub-pixels 114 can be rebinned before readout, as shown in FIGS. 7-8, thereby avoiding unnecessary electronic noise penalty. Conversely, in other approaches, shown in FIGS.

9-10, digital rebinning is performed after readout (i.e., the signal for each sub-pixel is read out and then rebinned), incurring an electronic noise penalty for each sub-pixel readout. A further option is to perform analog summing on the readout ASIC prior to conversion to digital signals. Such an approach may reduce some sources of noise, but not other.

Turning to FIG. 7, the charge from the large sub-pixel 114A and small sub-pixel 114B associated with each pixel 86 (e.g., a 1 mm×1 mm pixel) is obtained from a readout front-end 130 in accordance with a first binning scheme. The readout front-end 130 can then be summarized and digitized 132 to obtain a measurement for the pixel 86.

In the next (i.e., alternating) readout operation, and turning to FIG. 8, the respective sub-pixels 114 are buffered with the opposing adjacent sub-pixel, in accordance with a second binning scheme, so as to be reading a different effective pixel 120 that is spatially offset from the first pixel 86. That is, a given large sub-pixel 114A is binned (to readout front-end 130) with the adjacent small sub-pixel 114B opposite the small sub-pixel with which it was buffered in the previous read operation. The readout front-end 130 is then summarized and digitized 134 to obtain a measurement for the effectively offset (i.e., wobbled) pixels 120. As noted above, in certain such implementations a noise penalty is minimized due to the binning operations occurring before digitized signal readout 132, 134. Though the depicted examples show sub-pixels of different sizes, in other implementations, such as with respect to the sub-pixel configuration shown in FIG. 6, the sub-pixels may be equal in size.

Figure 9:
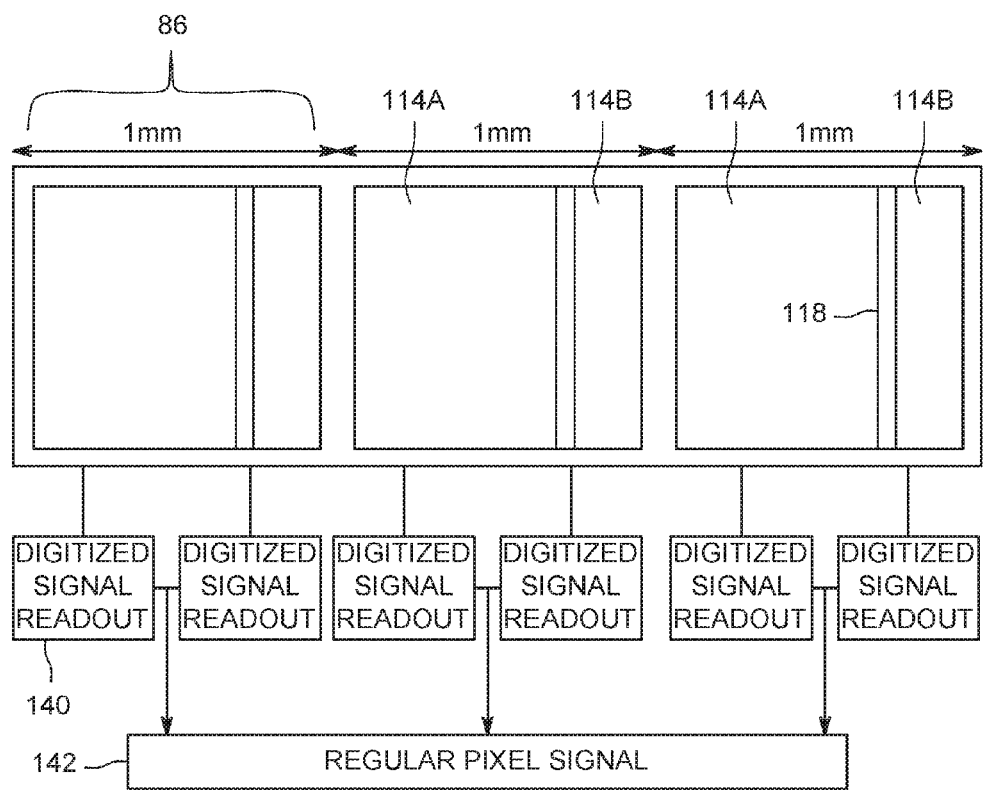
FIG. 9 depicts a first readout configuration for a detector in regular readout mode, in accordance with aspects of the present disclosure.
Figure 10:
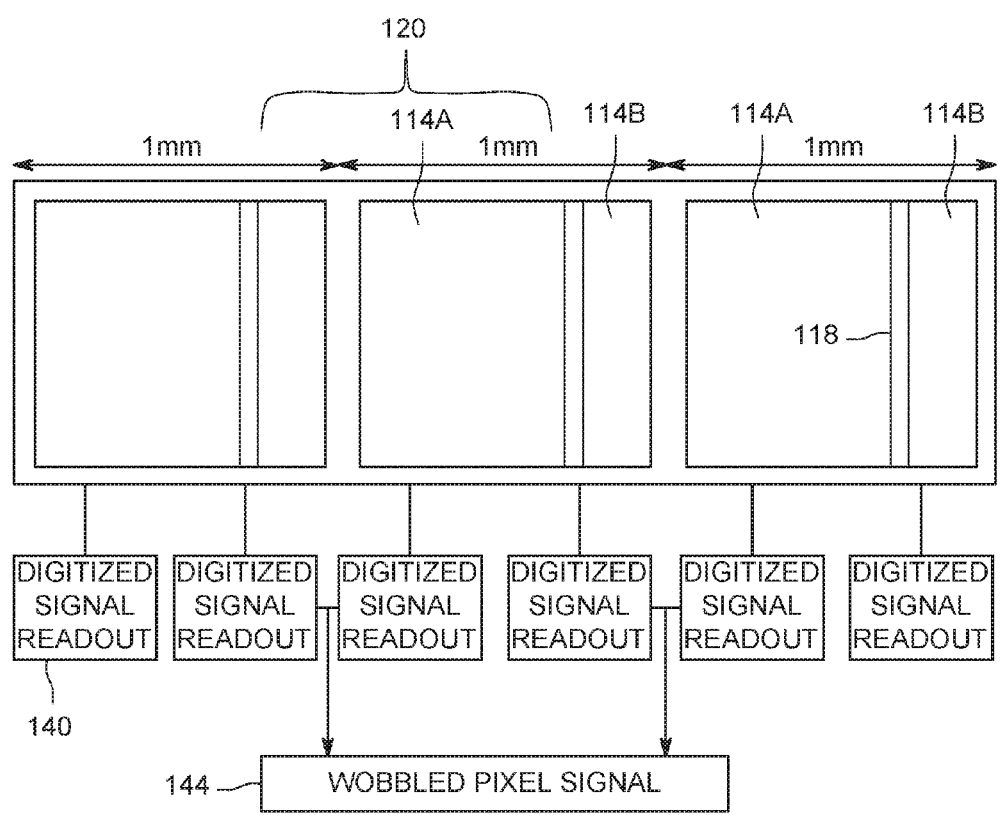
FIG. 10 depicts a second readout configuration for a detector in wobble readout mode, in accordance with aspects of the present disclosure.

Conversely, turning to FIGS. 9 and 10, in other implementations digital rebinning may occur after readout of each sub-pixel 114. In this example, each sub-pixel 114 is readout and digitized 140 in the normal manner and combined after readout. Turning to FIG. 9, the charge from the large sub-pixel 114A and small sub-pixel 114B (or equally sized sub-pixels 114C) associated with each pixel 86 (e.g., a 1 mm×1 mm pixel) is separately read out. The values readout are then subsequently combined 142 in accordance with a first combination scheme to obtain measurements for the pixels 86.

In the next (i.e., alternating) readout operation, and turning to FIG. 10, the respective sub-pixels 114 are again separately readout and digitized 140, but combined in a second combination scheme to obtain measurements for the spatially offset pixels 120.

That is, the readout value for a given large sub-pixel 114A is combined with the readout value for an adjacent small sub-pixel 114B opposite the small sub-pixel with which it was combined in the previous read operation. This second combination of readout values corresponds to a measurement for the effectively offset (i.e., wobbled) pixels 120. As noted above, in certain such implementations a noise penalty may be present that is associated with the readouts 140. Though the depicted examples show sub-pixels of different sizes, in other implementations, such as with respect to the sub-pixel configuration shown in FIG. 6, the sub-pixels may be equal in size.

Turning to FIG. 11, a circuit-type view is depicted of one electrical layout for a detector-based wobble read out. In this example, a sub-pixel arrangement similar to that shown in FIG. 4 is utilized so as to simplify presentation, though it should be appreciated that the described approach will also be suitable for use with other sub-pixel configurations, including the configurations shown in FIGS. 5 and 6.

In the depicted implementation, each sub-pixel 114 is readout via two paths, a first readout path (shown with shading) corresponding to a regular pixel readout and a second readout path (shown without shading) corresponding to a wobble readout path corresponding to a spatially offset pixel by combination of different adjacent sub-pixels 114. A controller 150 controls which readout path, the first and/or second, is active at a given time during a scan operation where a detector-based wobble is desired.

The depicted readout paths for each sub-pixel 114 include an amplifier 152 for amplifying the acquired signal from the respective sub-pixel 114 and a capacitor 154. The capacitors 154 may be used to integrate the signals from a sub-pixel readout operation and may be used to store an acquired signal until such time as it is needed for combination with the signal from an adjacent sub-pixel 114 to derive a signal corresponding to a normal pixel or wobble pixel, depending on the path specified by the controller 150. The simultaneous readout of the regular and wobble signal are, in certain implementations, achievable with the depicted design.

By way of example, three sub-pixels of FIG. 11 are shown and denoted as smaller sub-pixel 160 which along with larger sub-pixel 162 forms a pixel unit. In an adjacent pixel, smaller-sub-pixel 164 is also adjacent larger sub-pixel 162. Alternatively, as with respect to the geometric arrangement depicted in FIG. 6, the sub-pixels may be substantially equal in size. These three sub-pixels are each readout by separate respective readout paths that include amplification and storage circuitry (i.e., respective amplifiers 152 and capacitors 154) which allow the charge acquired at a given sub-pixel to be stored for subsequent combination and readout.

In this example, during a regular readout operation, the signals from sub-pixels 160 and 162 are combined (i.e., summed) in a first buffer 168. The summed signal converted from an analog signal to a digital signal at ADC 170 and read out to downstream signal processing circuitry.

Conversely, in the subsequent, alternating wobble readout operation, the signal from the larger sub-pixel 162 is summed in a second buffer 174 with adjacent sub-pixel 164 prior to analog-to-digital conversion, thereby generating a summed signal corresponding to wobble pixel spatially offset from the regular pixel readout in the prior operation. This analog summed signal is converted to a digital signal at respective ADC 170 and provided to downstream signal processing circuitry. In this manner, by alternating between readout paths the respective charges of sub-pixels 114 may be combined in an alternating and pairwise manner with different adjacent sub-pixels so as to generate outputs corresponding to different, spatially distinct and offset pixel areas during a scan operation. In this manner, a detector-based wobble effect can be introduced using the electronic readout mechanisms of the detector 28 as opposed to physically alternating the focal spot location on an X-ray source target.

Figure 11A:
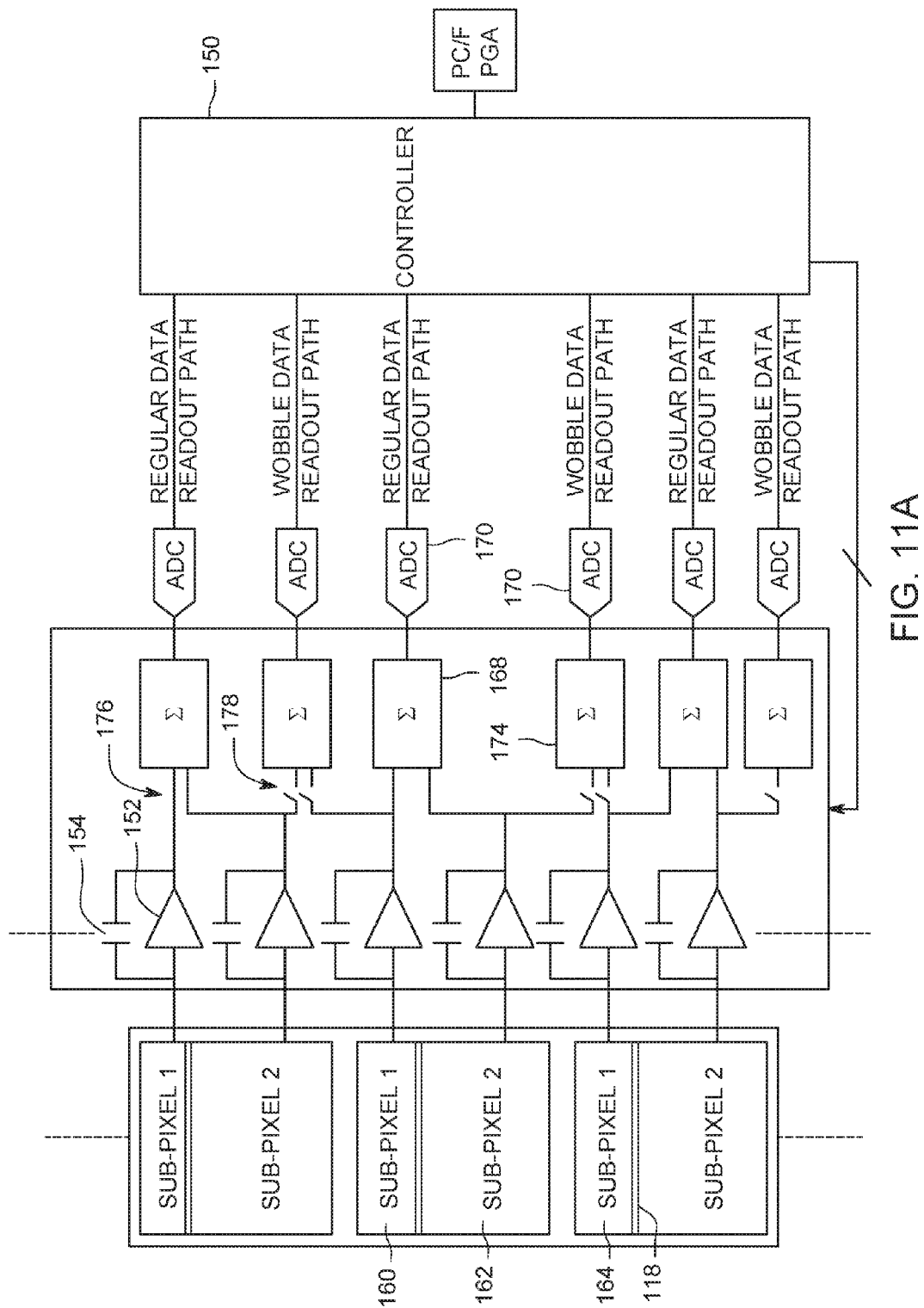
FIG. 11A depicts the circuit-based view of FIG. 11 in a normal pixel readout arrangement, in accordance with aspects of the present disclosure.
Figure 11B:
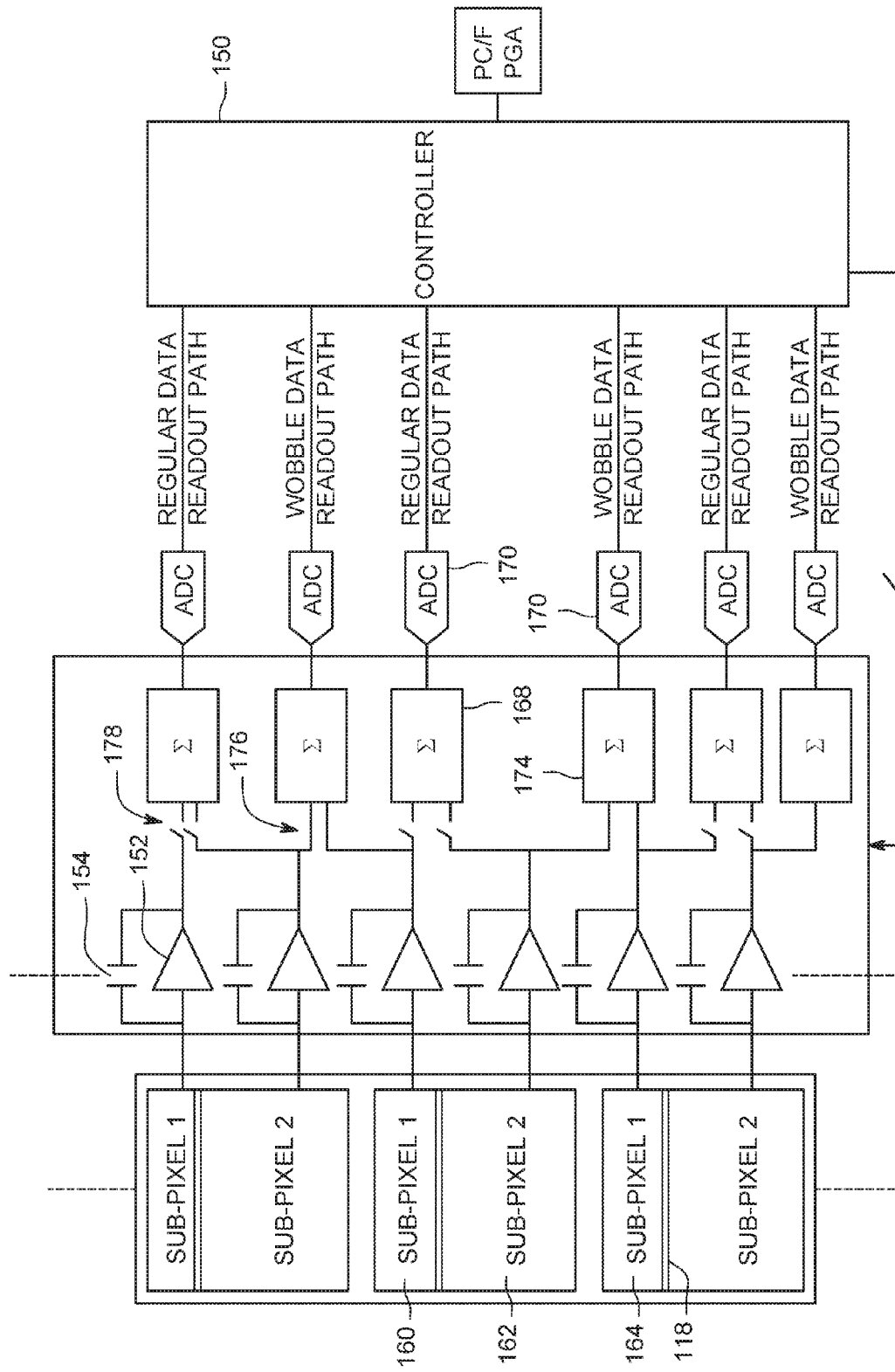
FIG. 11B depicts the circuit-based view of FIG. 11 in a wobble pixel readout arrangement, in accordance with aspects of the present disclosure.

With the circuit of FIG. 11, in mind, FIGS. 11A and 11B depict configurations of this circuit in a regular or normal pixel readout operation (FIG. 11A) and a wobble pixel readout operation (FIG. 11B). In particular, as shown in FIG. 11A, closed switches 176 cause two sub-pixels 160, 162 of a pixel being summed together, corresponding to a normal pixel readout signal. In the depicted example, the open switches 178 prevent summing of the large sub-pixel 162 of a given pixel with the smaller-sub-pixel 164 of the adjacent pixel. Conversely, as shown in FIG. 11B, in wobble mode the state of the switches is reversed, with the closed switches 176 causing summing of the large sub-pixel 162 of a given pixel with the smaller-sub-pixel 164 of an adjacent pixel. In the depicted example of FIG. 11B, the open switches 178 prevent summing of the large sub-pixel 162 and smallersub-pixel 160 of the same pixel. Though the depicted examples show sub-pixels of different sizes, in other implementations, such as with respect to the sub-pixel configuration shown in FIG. 6, the sub-pixels may be equal in size and non-rectangular in shape, as shown in both FIGS. 5 and 6.

Figure 12:
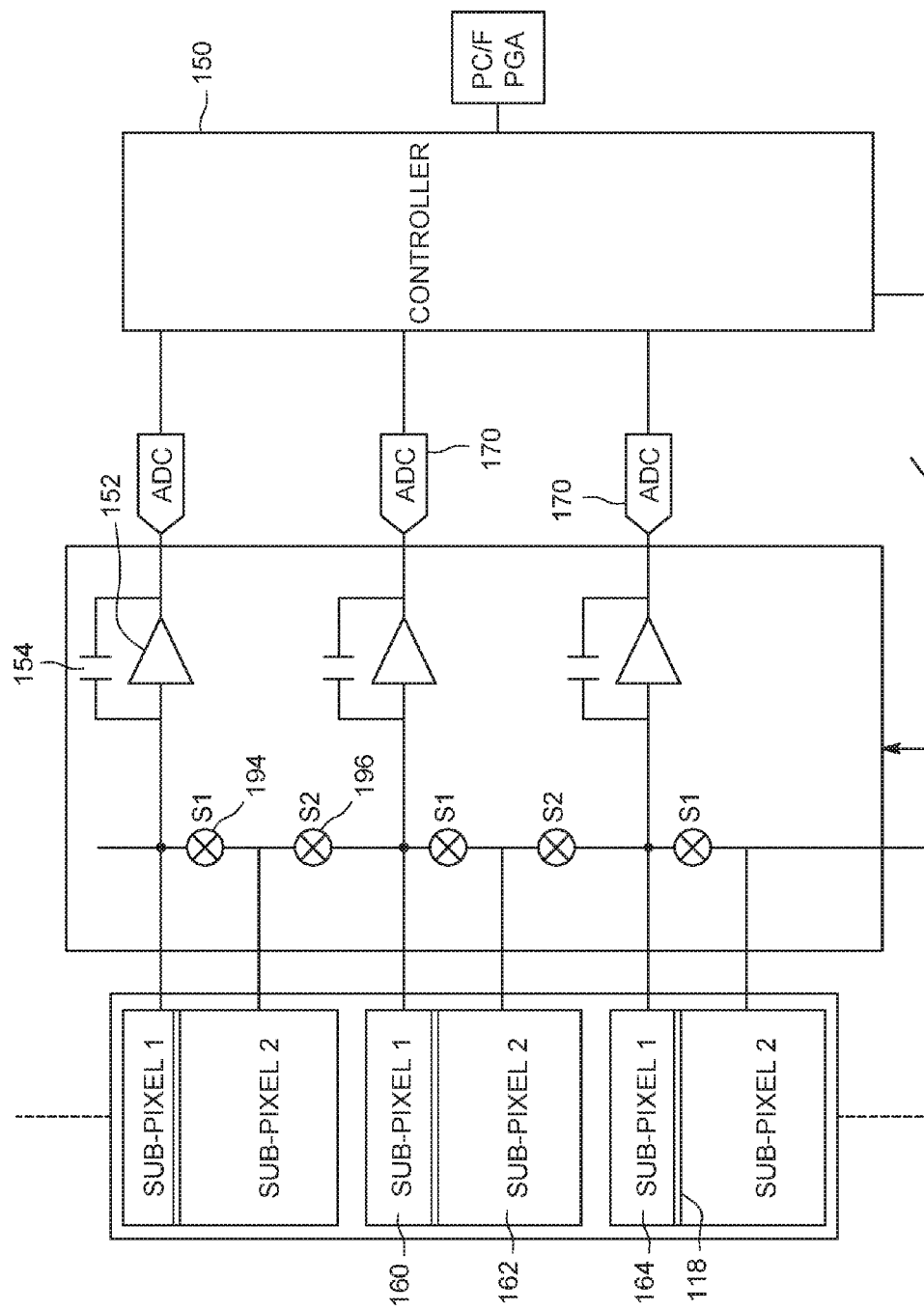
FIG. 12 depicts an alternative circuit-based view of the readout arrangement for a detector, in accordance with aspects of the present disclosure.

While FIGS. 11-11B depict one circuit-based example of the present approach, FIG. 12 depicts an alternative arrangement of a switch-based detector wobble approach which uses switches to select between the regular and wobble readout. This approach can be combined with integrated electronics on the light imager panel, as discussed above with respect to FIG. 3, to further reduce electronic noise introduced by binning the signal. In the configuration shown in FIG. 12, the circuit switches (i.e., via first set of switches 194, and second set of switches 196) between regular and wobble pixel readout. The signals are summed prior to reaching the readout front end, helping to reduce electronic noise. In the depicted example, the first set of switches 194 when closed corresponds to a normal pixel readout operation while the second set of switches 196 when closed corresponds to a wobble pixel readout operation. Only one set of switches is closed at a time during operation.

It should be noted however that the detector-based wobble approach discussed herein may be used in combination with focal-spot wobble techniques in which the X-ray focal spot is spatially shifted, such as between two locations Technical effects of the invention include a detector and ASIC design that allows detector-based wobble using an electronic control scheme. In one implementation, each detector pixel is divided into sub-pixels. The readout of the sub-pixels can be binned with minimal noise penalty to enable the detector wobble without physically shifting the detector or alternating the physical focal spot location, though, as discussed herein alternation of the focal spot location may be used in conjunction with the present approach to further improve in-plane imaging resolution.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A radiation detector, comprising:
   plurality of pixels, each pixel comprising:
      scintillator material that emits optical photons when exposed to X-rays;
      at least two photodetector elements, each photodetector element corresponding to a sub-pixel of the respective pixel, wherein each photodetector element is configured to generate electrical signals in response to the emitted optical photons that impact respective photodetector elements; and
   at least two signal summing circuits comprising at least one amplifier and at least one capacitor coupled to the at least one amplifier, wherein the at least one amplifier and the at least one capacitor are configured to simultaneously perform a regular pixel data readout and a wobble pixel data readout, wherein in the regular pixel data readout, analog signals from sub-pixels within the same pixel are combined, and in the wobble pixel data readout, analog signals from sub-pixels in different pixels are combined.

2. The radiation detector of claim 1, wherein each pixel comprises two sub-pixels.

3. The radiation detector of claim 2, wherein the two sub-pixels are differently sized such that a first sub-pixel is smaller in area than a second sub-pixel.

4. The radiation detector of claim 1, wherein the sub-pixels are further defined b at least one straight cut through the pixels forming at least one triangular corner sub-pixel within each pixel.

5. The radiation detector of claim 1, wherein each signal summing circuit of the at least two signal summing circuits comprises a readout buffer coupled to the at least one amplifier and the at least one capacitor.

6. The radiation detector of claim 1, wherein the at least one capacitor is configured to store signal from the respective sub-pixel.

7. A method for acquiring signals from a radiation detector, comprising:
   reading out a plurality of sub-pixels of a radiation detector, in which:
   during a regular readout operation, separately acquiring a first analog signal from a first sub-pixel and a second analog signal from a second sub-pixel adjacent to the first sub-pixel in a first direction and summing the first analog signal and the second analog signal to generate a summed regular pixel digitized signal; and
   during a wobble readout operation, separately acquiring a fourth analog signal from the first sub-pixel and a third analog signal from a third sub-pixel adjacent to the first sub-pixel in a second direction and summing the fourth analog signal and the third analog signal to generate a summed wobble pixel digitized signal, wherein the first sub-pixel and the third sub-pixel are within different pixels, and
   wherein the regular readout operation and the wobble readout operation are performed simultaneously via at least two signal summing circuits comprising at least one amplifier and at least one capacitor coupled to the at least one amplifier.

8. The method of claim 7, further comprising storing one or more of the first signal, second signal, third signal, or fourth signal in the at least one capacitor during the readout process.

9. The method of claim 7, wherein summing the signals comprises transferring the signals to be summed to an analog to digital convertor.

10. The method of claim 7, wherein the first sub-pixel and the second sub-pixel are within the same pixel.

11. The method of claim 7, wherein the regular readout operation and the wobble readout operation are performed simultaneously over a plurality of view angles about an imaging volume.

12. A radiation detector comprising:
   a plurality of pixels, each pixel divided into a first sub-pixel and a second sub-pixel; and
   a readout path comprising at least one amplifier and at least one capacitor coupled to the amplifier for each first sub-pixel and second sub-pixel to facilitate simultaneous readout of signals in a first state and a second state, wherein in the first state the outputs of the first sub-pixel and the second sub-pixel of the same respective pixels are combined and in the second state outputs of the first sub-pixel and the second sub-pixel of different pixels are combined.

13. The radiation detector of claim 12, further comprising a plurality of straight cuts dividing the pixels into respective first sub-pixels and second sub-pixels.

14. The radiation detector of claim 12, wherein the sub-pixels are further defined by at least one straight cut through the pixels forming at least one triangular corner sub-pixel within each pixel.

15. The radiation detector of claim 12, wherein each sub-pixel readout path is separated to a first readout path corresponding to a regular data readout path and a wobble data readout path.

\* \* \* \* \*